United States Patent
Zhang

(10) Patent No.: US 11,136,378 B2
(45) Date of Patent: Oct. 5, 2021

(54) METHODS OF CURING HBV INFECTION AND PROVIDING COMPLETE PROTECTION AGAINST HBV INFECTION

(71) Applicant: Yong-Yuan Zhang, Germantown, MD (US)

(72) Inventor: Yong-Yuan Zhang, Germantown, MD (US)

(73) Assignee: HBVtech LLC, Frederick, MD (US)

(*) Notice: Subject to any disclaimer, the term of this patent is extended or adjusted under 35 U.S.C. 154(b) by 17 days.

(21) Appl. No.: 15/354,043

(22) Filed: Nov. 17, 2016

(65) Prior Publication Data

US 2017/0152303 A1    Jun. 1, 2017

Related U.S. Application Data

(60) Provisional application No. 62/260,717, filed on Nov. 30, 2015.

(51) Int. Cl.
| | |
|---|---|
| *C07K 16/08* | (2006.01) |
| *A61K 39/42* | (2006.01) |
| *A61K 45/06* | (2006.01) |
| *A61K 39/00* | (2006.01) |

(52) U.S. Cl.
CPC ............ *C07K 16/082* (2013.01); *A61K 45/06* (2013.01); *A61K 2039/505* (2013.01); *A61K 2039/545* (2013.01); *C07K 2317/76* (2013.01)

(58) Field of Classification Search
None
See application file for complete search history.

(56) References Cited

U.S. PATENT DOCUMENTS

| 6,288,033 B1 * | 9/2001 | Leung | A61K 38/2292 |
| | | | 514/21.2 |
| 7,785,595 B2 * | 8/2010 | Dagan | A61K 9/0019 |
| | | | 424/141.1 |
| 2003/0096403 A1 * | 5/2003 | Hong | C07K 16/082 |
| | | | 435/345 |
| 2007/0027099 A1 * | 2/2007 | Lin | C12N 15/86 |
| | | | 514/44 A |
| 2007/0264646 A1 * | 11/2007 | Maki | C12Q 1/706 |
| | | | 435/5 |

OTHER PUBLICATIONS

Michel et al. (PNAS, 1995, vol. 92, p. 5307-5311).*
Balaz et al. (Nature Biotechnology, 2013, vol. 31, p. 647-655).*
Maura Dandri,Jorg Petersen, Chimeric mouse model of hepatitis B virus infection, J. of Hepatology 2012 Vol. 56, 493-495.
Alter et al. Hepatology, A Research Agenda for Curing Chronic Hepatitis B Virus Infection, vol. 67, No. 3 2018.
Lok, et al., Hepatitis B Cure: From Discovery to Regulatory Approval, Hepatology vol. 66, No. 4, 2017.
Robério Amorim de Almeida Pondé, Archives of Virology (2019) 164:2645-2658.
U.S. Department of Health and Human Services Food and Drug Administration: Considerations for the Design of Early-Phase Clinical Trials of Cellular and Gene Therapy Products.
Santora et al. Analytical Biochemistry 299, 119-129 (2001).
Oda et al. in Molecular Immunology 47 (2009) 357-364.
Farajnia et al., Journal of Immunopharmacology and Immunotoxiology, 2014; 36(5), 297-308.
Malpiedi et al. Journal of Process Biochemistry, 2013, 48: 1241-1251.

* cited by examiner

*Primary Examiner* — Agnieszka Boesen

(57) ABSTRACT

Disclosed are the methods of curing HBV infection and providing complete protection against HBV infection in a simplified HBV immunization schedule. The mechanistic basis for curing HBV infection is founded on the understanding that hepatitis B virus infection is established and prolonged by new rounds of infection with continuously produced viruses, which are not fully neutralized because of insufficient endogenous neutralizing antibodies. The methods of curing HBV infection including chronic HBV infection are aimed to block new rounds of HBV infection. The guidelines for establishing treatment regimens for curing HBV infection, include production or administration of sufficient level of HBV neutralizing antibodies in treated patients. Among the many different possibilities contemplated, the sufficient level of HBV neutralizing antibodies is expressed and maintained by the single injection of the HBV therapeutics that comprises non-replicating viruses or vectors encoding HBV neutralizing antibodies or by multi-injection of exogenous HBV neutralizing antibodies.

12 Claims, 9 Drawing Sheets

METHODS OF CURING HBV INFECTION AND PROVIDING COMPLETE PROTECTION AGAINST HBV INFECTION

PRIORITY

This application claims the priority under 35 U.S.C. § 119(e) to U.S. provisional application No. 62/260,717 filed Nov. 30, 2015.

FIELD OF THE INVENTION

The present invention relates generally to the field of treatment and prevention of hepatitis B virus (HBV) infection.

BACKGROUND OF THE INVENTION

I. HBV Infection and Current Therapy

It is estimated that 240 million people are chronically infected with hepatitis B virus (HBV). Chronic HBV infection can cause ongoing liver injury that leads to fibrosis, cirrhosis and hepatocellular carcinoma (HCC). More than 780,000 patients die of complications of chronic HBV infection each year(Lozano et al., 2012; WHO, 2015).

New HBV infection keeps emerging and approximately 4.5 million of new HBV infections occur each year (Franco et al., 2012).

I.1. No Antiviral Therapy for Acute HBV Infection or Patient with HBsAg Positive for Less than 6 Months.

HBV infection occurs in both young children vertically transmitted from their HBV positive mothers, and adults horizontally transmitted by close contact, contaminated blood and body fluids and sharing needles and equipment. Outcomes of HBV infection are age-dependent. HBV infection in 90% of infected young children is persistent (>6 months) while HBV infection in 90% of adults is transient (<6 months). Patients who eventually resolve HBV infection can experience acute liver injury, a clinical course that can last several months (Trepo et al., 2014).

There is no antiviral treatment for individuals who are HBV acutely infected or are hepatitis B surface antigen (HBsAg) positive for less than 6 months(European Association For The Study Of The, 2012; Liaw et al., 2008; Lok and McMahon, 2009). Consequently, HBV infection in more than 90% of infected young children and 10% of infected adults becomes chronic, which constantly replenish and expand chronic HBV infected population.

There is a need for methods and therapeutics that treat patients with acute HBV infection or HBsAg positive for less than 6 months.

I.2. Chronic HBV Infection and Current Therapy

Currently, FDA approved two classes of antivirals treating chronic HBV infection (HBsAg positive for at least 6 months). One is nucleos/tide analogues (NAs) that are orally administrated and require daily medication for multi years to suppress HBV replication. The other is Interferon/pegylated Interferon that are injected three times or once a week for 48 weeks. The treatment with interferon is poorly tolerated because of interferon-induced reduction of platelet count (thrombocytopenia). The NAs, especially the early generation of NAs, which are still widely prescribed in developing countries, cause high frequency of drug resistance. Both modalities rarely clear chronic HBV infection after long term treatment (Ghany and Doo, 2009; Kwon and Lok, 2011). Chronic HBV infection is now considered incurable, an indefinite treatment, just like treating other chronic diseases including diabetes, is required.

What is more disappointing is that current antiviral therapy is only suitable for 10-15% of chronic HBV infected patients who have relatively high level of HBV DNA and elevated alanine aminotransferase (ALT) or histology evidence of liver injury(European Association For The Study Of The, 2012; Liaw et al., 2008; Lok and McMahon, 2009).

The remaining 85-90% of chronic HBV infected patients who have normal ALT, are not recommended for antiviral treatment. Those patients can experience unpredictable flare-ups of liver injury, which can result in liver failure with up to 70% mortality (Olson and Kamath, 2011; Sarin et al., 2014). There is no effective treatment once the chronic infected patients undergo acute exacerbations of liver disease.

Efforts have been directed to developing different therapeutics against chronic HBV infection. For instance, HBV neutralizing antibodies had been used for treating chronic HBV infection in clinical trials (Eren et al., 2000; Galun et al., 2002; Heijtink et al., 2001; McMahon et al., 1992). Those trials established the safety profile of neutralizing antibodies, and showed the efficacy of neutralizing HBV particles, which transiently rendered both HBsAg and HBV DNA undetectable in the blood if a sufficient level of neutralizing antibodies was administrated.

However, such efficacy was not sustainable and both HBsAg and HBV DNA returned to the pretreatment levels once the serum level of the injected neutralizing antibodies fell (Eren et al., 2000; Galun et al., 2002). Those clinical trials did not move beyond the early phase, probably because no sustainable efficacy was noted. More critically, there has been a lack of rationale to convince the field that a treatment with HBV neutralizing antibodies is fundamental sound and effective.

Currently HBV neutralizing antibodies or hepatitis B immunoglobulin (HBIG) are only indicated for HBV prophylaxis, not for HBV treatment(Habib and Shaikh, 2007).

There are two rationales that discourage use of HBV neutralizing antibodies for treating chronic HBV infection.

One is current mechanisms that explain chronic HBV infection, disfavor using HBV neutralizing antibodies for treating chronic HBV infection. The current pathogenesis theory describes that chronic HBV infection is a consequence of the host's insufficient specific immunity that can't kill all HBV infected cells (Chisari and Ferrari, 1995; Chisari et al., 2010). The current theory implies that chronic HBV infection is an extension of initial HBV infection and is not curable unless all HBV infected cells were killed. Since HBV neutralizing antibodies primarily neutralize extracellular HBV particles and have little impact on HBV infected cells, a treatment of chronic HBV infection with HBV neutralizing antibodies is viewed as ineffective or nonessential in HBV field.

However, there have been many reports in the art that described frequent emergence of HBV mutants including pre-core, core, pre-S and S variants, while the initial or earlier viruses were being eliminated, as dominant viral populations in patients/animals with HBV infection. Those available results directly disapprove the current theory underlying chronic HBV infection. However, the HBV field has not yet come to elevate the consensus findings to a new theory that can replace the current view and that can guide better understanding how HBV infection becomes chronic, and helps devise an effective treatment strategy.

The other is no sustained treatment efficacy as mentioned above. The unstained treatment efficacy with HBV neutralizing antibodies was caused by ineffective regimens in which both dose and frequency of administration of HBV neutralizing antibodies were arbitrarily determined (Eren et al., 2000; Galun et al., 2002) or suggested (WO2006076640A1,WO2009069917A1). Both serum HBsAg and HBV DNA can transiently become undetectable after a sufficient amount of anti-HBs was given, but the timing and dose of next administrations were subjectively predetermined regardless of dynamic changes in the relative amounts of HBV particles and the injected anti-HBs antibodies in treated subjects, and it was often too late in the time of next injections or too small in the next doses to sustain the anti-HB s level high enough to constantly neutralize HBV particles, resulting in the bounce back of both HBsAg and HBV DNA in the serum.

The treatment regimens with anti-HBs antibodies in the reported clinical trials were not designed to maintain HBV neutralizing antibodies at sufficient level that constantly keep the serum HBV particles undetectable in treated individuals.

People also tried to treat chronic HBV infection with HBV vaccines either consisting of viral envelope proteins or DNA plasmids that express viral proteins, but no significant benefits with HBV vaccine treatment were observed (Couillin et al., 1999; Kosinska et al., 2010). It has not provided a convincing rationale that can justify such treatment because patients with chronic HBV infection have, as a matter of fact, been constantly immunized with HBV particles. The fundamental immunodeficiency in patients with full-blown HBV infection is not short of immunization or vaccination, but an absence of capacity to produce sufficient level of HBV neutralizing antibodies following the HBV exposure.

There is an urgent need for an improved understanding of HBV infection, and for methods and therapeutics for improved HBV treatment.

II. Current HBV Immunization Schedule and Unsatisfactory Protection

Immunization of newborns with HBV vaccine starting within 24 hours after birth, is recommended by World Health Organization (WHO) (WHO, 2015) and Centers for Diseases Control and Prevention (CDC)(CDC, 2005) and mandated by the law in many countries.

Current HBV immunization of newborns whose mothers are HBV positive or are in an unclear status of HBV infection at the time of delivery, consists of 4 injections at 3 time points. It starts with injection of both hepatitis B immunoglobulin (HBIG) that contains HBV neutralizing antibodies to provide passive immunization, and HBV vaccine within 24 hours after birth. The remaining two injections are scheduled in the $1^{st}$ and $6^{th}$ month after the birth dose.

However, the current HBV immunization scheme results in 5-15% protection failure in immunized newborns because the titer of HBV neutralizing antibodies in the injected HBIG was not sufficiently high to neutralize all hepatitis B viruses transmitted by the mothers who carried high load of HBV viruses in the blood(Lee et al., 2006; Zou et al., 2012). The anti-HBs in the circulation following one-time injection is depleted quickly when binding to HBV particles. The injected HBIG does not provide a sustained level of anti-HBs antibodies, contributing to the failure in HBV immunization. The immunization failure alone results in approximately one million new HBV infections of infants each year, and 90% of them become chronic. In addition, HBIG is expensive because it is prepared from pooled human plasmas. HBIG is also potentially hazardous because the pooled human plasmas may contain unknown pathogens.

To mitigate the failure of HBV immunization of newborns, physicians now try to treat the HBV infected mother during the pregnancy with antivirals for several months to lower serum HBV concentration before birth(Lamberth et al., 2015). This approach still results in the immunization failure (Chen et al., 2015). It does not directly address the fundamental problem of insufficient neutralizing antibodies in pregnant women and immunized newborns, is costly ($500-$3000 for 3-month therapy) and carries the risk to unborn baby because the impact of antiviral treatment on long term health of the drug exposed fetus, has not been established(Pan and Lee, 2013).

It is burdensome to fully comply HBV immunization schedule in which 3 or more injections must be given on three time points, especially in remote and poor villages of developing countries where birth rate is usually high. Multi-injection is intimidating and discourages people from active participation, contributing to significant gaps in immunization coverage, and increases difficulty to complete the schedule.

There is an urgent need for methods and prophylactics that improve HBV immunization efficacy and simplify immunization schedule.

All referenced patents and applications are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

SUMMARY OF THE INVENTION

In the present invention, methods are provided to turn currently incurable chronic HBV infection into a curable disease, and to turn insufficient neutralizing antibody production in individuals with HBV exposure or immunization or vaccination, into producing a long term sufficient level of neutralizing antibodies.

The invention first discloses that HBV infection is established and maintained through new rounds of infection with produced viruses in the same livers, which are not fully neutralized because of insufficient endogenous neutralizing antibodies in HBV infected individuals; it further discloses that maintaining sufficient level of HBV neutralizing antibodies is required for curing HBV infection; in preferred embodiments the sufficient amount of HBV neutralizing antibodies is produced and maintained by a single injection of the defective viruses into muscle cells that express and secret HBV neutralizing antibodies or by multi-injection of exogenous HBV neutralizing antibodies over time. It still discloses that the methods of curing HBV infection, blocking the HBV infected newborns, who are prone to chronicity of HBV infection, from becoming chronic and facilitating the acutely infected patients to establish early recovery. It additionally discloses that the single injection of the HBV therapeutics also functions as prophylactics to produce and maintain the sufficient level of HBV neutralizing antibodies, and to fully protect newborns and individuals at high risks from HBV infection.

Various objects, features, aspects, and advantages of the present invention will become more apparent from the following detailed description of preferred embodiments of the invention, along with the accompanying drawings.

○: Wild type virus; ●: Mutant virus; : HBV cccDNA

FIG. 2. The methods of establishing a complete and permanent viral clearance and curing HBV infection through maintaining sufficient level of HBV neutralizing antibody in treated subjects. A. Extrahepatic hepatitis B viruses are not neutralized and are infectious for new rounds of infection in absence of anti-HBs antibodies. The liver remains infected despite ongoing viral clearance; B. A sufficient amount of anti-HBs antibodies is expressed through the single injection of the HBV therapeutics (see FIG. 3) or administrated through multi-injection (see FIG. 4), which is greater than that of the extrahepatic viruses; C. Extrahepatic viruses are neutralized and removed that protects the liver from new rounds of infection while the liver keeps clearing viruses; D. A complete and permanent clearance of HBV from the liver is established through maintaining sufficient level of anti-HBs antibodies.

○: Wild type virus; ●: Mutant virus; Y: Anti-HBs antibody

FIG. 3. A schematic presentation of kinetic changes in serum levels of both HBsAg and expressed anti-HBsAg antibodies after a single injection of the HBV therapeutics that comprise the defective adeno-associated viruses (AAV) encoding HBV neutralizing antibodies. The serum levels of anti-HBs antibodies plotted herein represent a medium range of efficiency for expressing of the antibodies. Filled circle: anti-HBs antibodies; Open circle and broken line: HBsAg.

FIG. 4. A schematic presentation of regimen for constantly maintaining a sufficient level of anti-HBs antibodies through multi-injection. Next injections occur before the serum level of the anti-HBs antibodies fell below the level of the serum HBV particles. Please note: the dose and frequency of injection are determined based on actual serum level of HBsAg before each injection, not predetermined subjectively. Filled circle: anti-HBs antibodies; Open circle and broken line: HBsAg. Arrow indicates the time of injection of anti-HBs antibodies.

FIG. 5. Minimal genetic components required for encoding HBV neutralizing antibodies in a viral vector. The anti-HBs genes are cloned from individuals who produced anti-HBs antibodies or from the anti-HBs producing cell lines or from synthesized DNA fragments. VH: heavy chain variable region; CH: heavy chain constant region; VL: light chain variable region; CL: light chain constant region.

FIG. 6. Illustrating the expected outcomes in treated HBV infected patients who remain at acute phase of infection or are HBsAg positive for less than 6 months, with the methods of curing HBV infection.

FIG. 7. A comparison of the scope and outcomes of chronic HBV infected patients between the current therapy and the methods of curing HBV infection in the invention.

FIG. 8. A schematic presentation of current (A), improved HBV immunization schedules for infants borne to HBV positive mothers or individuals with exposure to HBV infection (B), and for infants borne to HBV negative mothers (C) in the present invention.

FIG. 9. A comparison of benefits and risks between the injection of HBIG and the single injection of the therapeutics that comprises AAV expressing the long-term sufficient level of HBV neutralizing antibodies.

DETAILED DESCRIPTION OF THE INVENTION

FIG. 1 generally depicts the understanding of mechanisms for chronic HBV infection in the art (A) and the understanding of the mechanisms for HBV infection in the invention (B). Two understandings differ fundamentally in following aspects:

The understanding in the art believes that a liver cell, once infected with HBV, will be persistently infected with initially infected hepatitis B virus unless this infected cell is killed by HBV specific CT8+ cytotoxic cells. If the specific T cell immunity in HBV infected patients is insufficient that could not kill HBV infected cells, then HBV infection becomes chronic (Chisari and Ferrari, 1995; Chisari et al., 2010). The understanding in the art implies that HBV infection, chronic HBV infection in particular, is an extension of the initial HBV infection. Chronic HBV infection can't be cured under the current theory unless all infected cells were killed, which is impossible.

The understanding disclosed in the inventive subject matter derived from a process in which the inventor transformed the observations of frequently emergent mutant virus infection following the initially or earlier infected viruses were being eliminated from livers in both experimental and clinical HBV infections, into new mechanisms for HBV infection. The essence of this understanding underscores that early infected hepatitis B viruses in infected livers are frequently eliminated, and the cells that had cleared the initial or earlier HBV, are reinfected with newly generated viruses. Such replacement of the earlier infected viruses in the liver can be completed in a few weeks (Pult et al., 2001; Zhang and Summers, 1999). Thus, HBV infection is not an extension of the initial infection, but it is established and maintained by new rounds of infection with produced viruses in the same livers, which are not completely neutralized because of insufficient endogenous neutralizing antibodies. The fundamental immunodeficiency in subjects with full blown HBV infection or chronic HBV infection is a lack of sufficient level of HBV neutralizing antibodies. Once new rounds of infection were blocked with the sufficient level of HBV neutralizing antibodies, a HBV-clearing liver will achieve a complete and permanent clearance. Thus, HBV infection including chronic HBV infection is curable with the methods of curing HBV infection in the invention.

Example 1

Wildtype virus was replaced by mutant virus in experimental infection. Duck hepatitis B virus (DHBV) and DHBV infected ducks are validated models for studying HBV infection. A group of ducks were experimentally infected with a mix of wildtype (WT) DHBV and mutant (MT) DHBV that only replicated at about 50% efficiency of WT replication. Because of significant replication advantage over mutant, WT quickly became dominant population and the mutant was about to disappear from the infected livers. However, we then observed an unexpected reversal in which WT was progressively eliminated and replaced by the mutant that became predominant or an only virus population in next 4-6 weeks (Zhang and Summers, 1999), suggesting that WT was being eliminated from the infected livers, and the WT clearing livers were then reinfected with the mutant.

Example 2

The same dynamic elimination of earlier virus populations was also reported in clinical HBV infection. for instance, WT was frequently eliminated and replaced by pre-core or core or pre-S or S mutants in untreated patients (Brunetto et al., 1991; Okamoto et al., 1994; Yamamoto et al., 1994), suggesting that HBV infected livers are no longer infected with the initially infected WT, but with the lately emerged mutants, and the recurrent infections prolong the course of HBV infection.

This dynamic elimination of the earlier virus populations also holds true for treated patients with antivirals. For instance, WT was frequently eliminated from treated livers, which were then reinfected with drug resistant mutants in nucleos/tide analogues (NAs) treated patients(Ghany and Doo, 2009; Locarnini and Bowden, 2010).

Taken together, HBV infection is not an extension of the initial infection, but is established and maintained with new rounds of infection.

Figure 1:
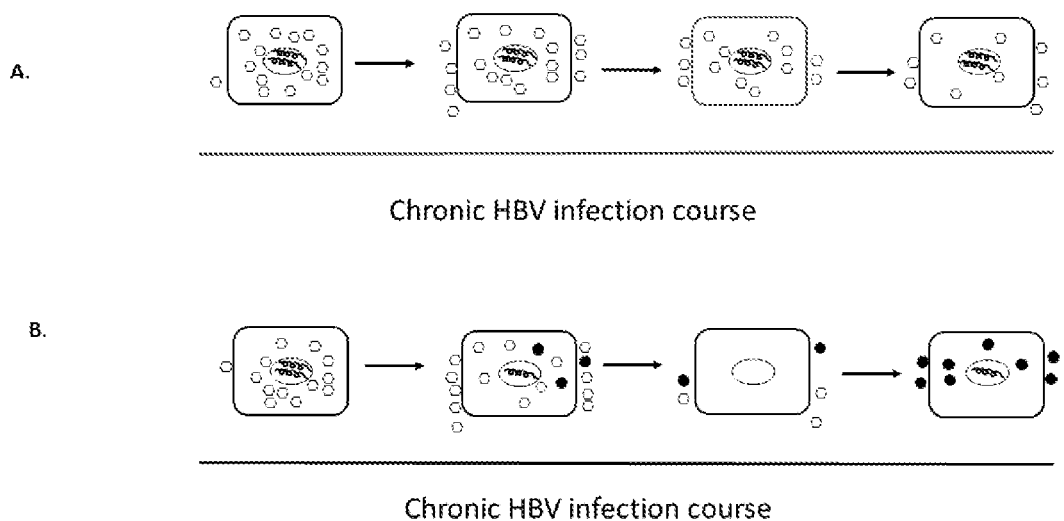
FIG. 1. Two understandings of HBV infection. A. Current understanding of chronic HBV infection in the art. Current theory suggests that HBV infection becomes chronic if HBV infected patients have insufficient immunity that can't clear HBV from infected cells or kill HBV infected cells. Liver cells, once infected with HBV, will remain infected with initially infected HBV in chronically infected patients. B. Understanding in the inventive subject matter. Initially infected HBV is cleared from infected cells, but virus-clearing cells are repeatedly infected with newly produced mutant (MT) virus and/or wild type (WT) virus. The course of HBV infection is prolonged by new rounds of infection, and chronic HBV infection is not an extension of the initial HBV infection.
Figure 2:
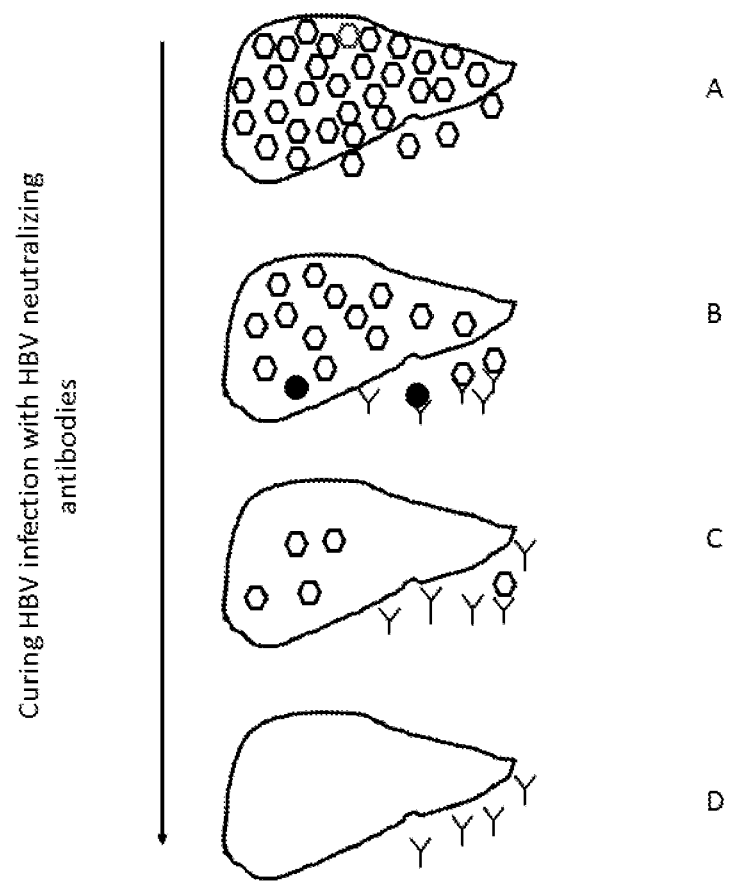

FIG. 2 outlines the methods for curing HBV infection, especially for chronic HBV infection. The methods of curing HBV infection are devised to constantly block new rounds of infection with sufficient level of HB V neutralizing antibodies.

The fundamental problem in HBV infection, highlighted by the mechanisms underlying HBV infection in the inventive subject matter, is the lack of the sufficient level of HBV neutralizing antibodies. Consequently, the achieved viral clearance in infected livers is not permanent because virus-clearing livers are not protected from new rounds of infection, which reverse gains in viral clearance and extend the course of HBV infection. To clear a full-blown HBV infection or chronic HBV infection, a providing of the sufficient and sustained level of HBV neutralizing antibodies is required.

HBV infected cells not only produce full viral particles, but also produce a huge pool of subviral particles (also called hepatitis B surface antigen or HBsAg). The ratio of full and subviral particles is 1:1000 to 1:10,000 (Ganem and Prince, 2004). The concentration of subviral particles can be as high as 10 µg/ml (Gerlich et al., 2007). Both particles are wrapped with the S protein, a major component of hepatitis B surface antigen(Patient et al., 2009). On the other hand, the amount of endogenous neutralizing antibodies is severely insufficient comparing the amount of subviral particles. Thus, the endogenous neutralizing antibodies are depleted mainly by subviral particles leaving a portion of full viral particles unneutralized and infectious(Trepo et al., 2014).

To completely block new rounds of HBV infection, we have to remedy the insufficient endogenous neutralizing antibodies in HBV infected subjects either through expanding the endogenous HBV neutralizing antibody production capacity or through administration of exogenous HBV neutralizing antibodies.

When treating HBV infected individuals with HBV neutralizing antibodies, a key guideline for treatment regimens is constantly maintaining sufficient level of HBV neutralizing antibodies. The sufficient level of HBV neutralizing antibodies is herein defined as a minimal amount that constantly keeps the all serum viral particles undetectable in treated subjects.

When a sufficient amount of HBV neutralizing antibodies is sustained, infectious viral particles will be neutralized and removed. It will quickly convert serum HBsAg positive to anti-HBsAg positive, an ideal outcome for treating HBV infection. Once converted to anti-HB s antibody positive, new rounds of HBV infection will be blocked. Uninfected cells and cells that had cleared HBV will stay uninfected, leading to a complete and permanent viral clearance in which all infected cells cleared HBV infection and continued to stay uninfected under the protection of the sufficient neutralizing antibodies. Then HBV infection has been cleared and cured.

HBV neutralizing antibodies not only neutralize the maternal HBV particles, but also enter fetal circulation to protect fetuses from intrauterine infection, and the carry over antibodies also protect newborns from perinatal infection when HBV positive pregnant women are treated with the sufficient and sustained level of HBV neutralizing antibodies.

Example 3

There is a clear relationship between appearance of anti-HBs antibodies and clearance of HBV infection. In evaluating the treatment efficacy in an animal model of HBV infection, chronic DHBV infected ducks were treated with DNA vaccines that encoded DHBV envelope or core proteins as monotherapy or in combination with a reverse transcriptase inhibitor (lamivudine). The seven of eight animals that had detectable anti-HBs antibodies, cleared chronic DHBV infection including DHBV covalently closed circular DNA (cccDNA) from infected livers (Thermet et al., 2008).

Example 4

It is well established that all resolved HBV infection including acute and chronic HBV infection is accompanied by appearance of anti-HBs antibodies (Trepo et al., 2014), because the anti-HBs antibodies protect livers from new rounds of infection and render ongoing viral clearance complete and permanent.

Example 5

HBV Immunization of HBV positive newborns is de facto a treatment of HBV infection with anti-HBs antibodies. Fetuses are frequently HBV infected through exchanges of blood components from their HBV positive mothers. Upon birth, those babies are already positive for both HBV DNA and HBsAg, suggesting an intrauterine HBV infection. Thus, when HBV positive newborns are administrated with HBIG (hepatitis B immunoglobulin), it represents a treatment of HBV infection with anti-HBs antibodies. It is well established that more than 90% of those babies with HBV perinatal infection become chronic. However, the HBV infected babies can be cured if a sufficient amount of HBV neutralizing antibodies is administrated and sustained. In a clinical study, 32 infants born to HBV positive mothers were immunized with both HBIG and HBV vaccine within 24 hours after birth and with two more injections at month 1 and 6. Seven months later, 17 of them cleared HBV infection and each of them had detectable anti-HBs antibodies. The 15 (47%) remained HB V infected, a significant reduction from 90% chronic HBV infection under the circumstances of no HBV immunization, and none of the infected 15 babies had detectable HBV neutralizing antibodies (personal communication).

In another study, 4 of 10 HBV positive newborns who were immunized with both HBIG and HBV vaccine after birth, had detectable anti-HBs antibodies 6 months later and they also cleared HBV infection while all of 6 infants became chronically infected with undetectable anti-HBs antibodies (Chen et al., 2015).

However, those results are only considered a success of preventing, but not treating of HBV infection with HBV neutralizing antibodies by the HBV field.

Example 6

A key mechanism that determines if a HBV infection is transient or persistent (chronic), is the level of HBV neutralizing antibodies in infected individuals. HBV infection in 90% of infected adult is transient, whilst becomes chronic in more than 90% of infected infants and young children because the high level of HBV neutralizing antibodies was produced and maintained in the infected adult subjects, but it was not in the infected young subjects (Zhang and Summers, 2004).

Figure 3:
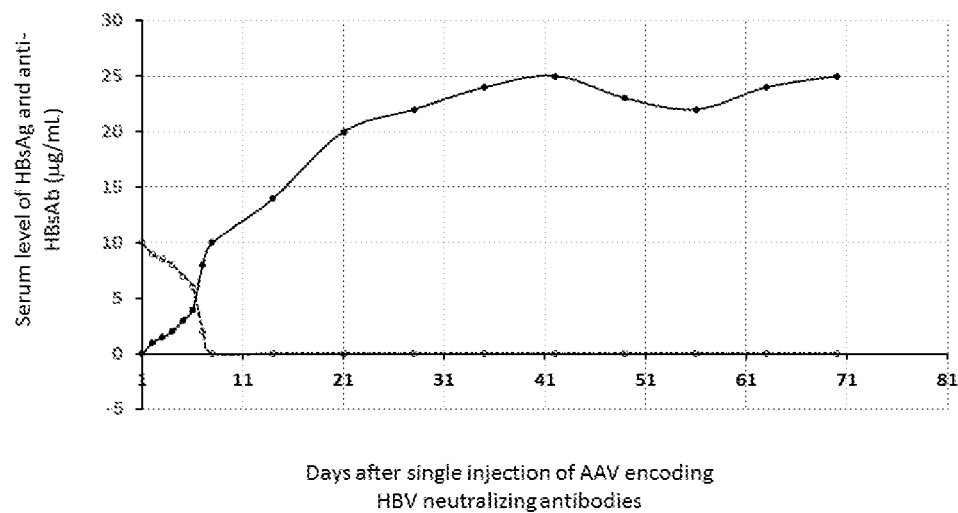

FIG. 3 shows an example for the methods of curing HBV infection with a single injection of the HBV therapeutics comprising AAV that produces a medium level of HBV neutralizing antibodies (greater than 10 µg/ml). The concentration of HBV neutralizing antibodies keeps increasing and exceeding the amount (10 µg/ml, considered a high end of serum HBsAg concentration) of HBsAg in about two weeks. The serum HBsAg level is progressively decreased, becomes undetectable and remains undetectable during the course of treatment. The level of the anti-HBs antibodies stays at a concentration of more than 10 µg/ml for three months or longer after the single injection. The long term sufficient level of anti-HBs antibodies neutralizes HBV particles and protects virus-clearing livers from new rounds of infection. A complete and permanent clearance of HBV from infected livers will be established, and then HBV infection is cured.

HBV field has not used the single injection of the therapeutics that comprises the defective viruses to express the long term sufficient level of HBV neutralizing antibodies for treating or curing HBV infection.

In the many possibilities contemplated, the dose for the single injection of the HBV therapeutics is determined by the antibody expression efficiency that is suggested by the manufacturer or is empirically determined by quantitatively detecting the serum level of the endogenously expressed anti-HBs antibodies. The detection kits are commercially available and procedures are well known for those skilled in the art. The guideline aims to make sure the sufficient level of anti-HBs antibodies that may consist of 1-10 µg/ml or higher or up to 100 µg/ml or even higher, is expressed to constantly keep the serum HBV particles undetectable.

The HBV therapeutics that comprises the defective viruses, is designed for a single injection to produce the long term sufficient level of anti-HBs antibodies. However, the therapeutics can be repeatedly injected under the circumstances that include, but not limit to: a failure of the first injection, insufficient dose of the first injection, only a single virus population contained in the first injection or inefficient expression of anti-HBs antibodies by the defective viruses. The number of injections is determined by effective level and neutralizing spectrum of the expressed anti-HBs antibodies.

In preferred embodiments, the defective viruses comprise a single virus population encoding one anti-HBs antibody or antibody fragment targeting an epitope of HBV envelope proteins. In more preferred embodiments, the defective viruses comprise mixed virus populations, each of which encode one anti-HBs antibody or antibody fragment targeting one epitope of HBV envelope proteins to provide broad neutralizing spectrum and maximal efficiency and to prevent mutants from escaping neutralization.

Figure 4:
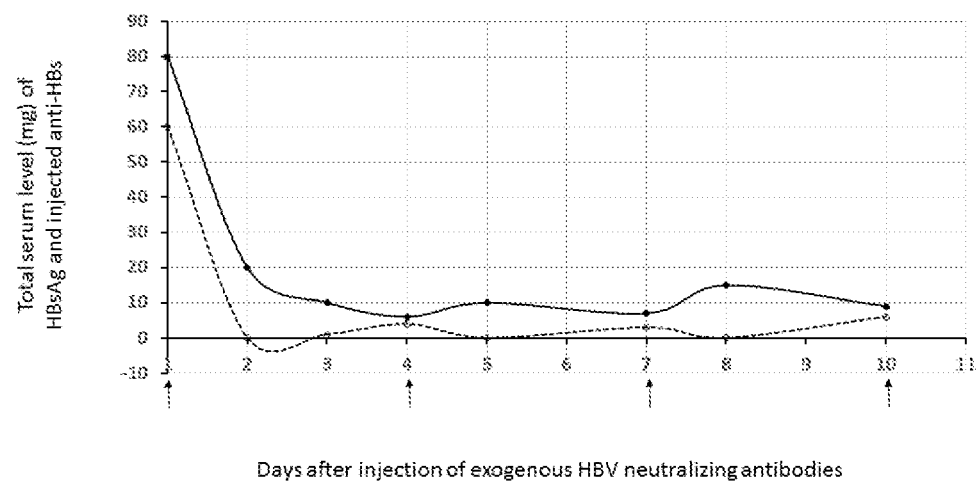

FIG. 4 shows an example for the methods of curing HBV infection with multi injection of exogenous HBV neutralizing antibodies. To constantly maintain the sufficient amount of HBV neutralizing antibodies and to eliminate possibility that the level of HBV neutralizing antibodies may fall below the serum level of HBV particles, the dose of exogenous antibodies should be determined based on the serum level of HBV particles before each injection and the principle for the dose determination is that the amount of injected antibodies should be greater than total amount of HBV particles in the serum. Next injections should be scheduled before the level of HBV neutralizing antibodies fall below the serum levels of HBV particles until all HBV infected cells clear HBV.

Example 7

The dose and frequency of injecting exogenous antibodies in the art were arbitrarily determined (Eren et al., 2000; Galun et al., 2002; McMahon et al., 1992) and such methods inevitably resulted in the treatment failure because HBV became unneutralized and infectious and caused new rounds of infection once the level of HBV neutralizing antibodies fall below the serum level of HBV particles.

Figure 5:
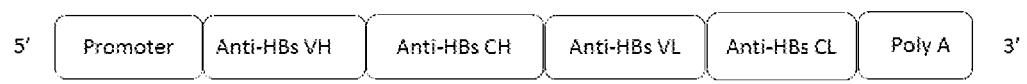

FIG. 5 shows minimal genes encoding anti-HBs antibodies in viral vectors. The viral vectors are a DNA viral vector including, but not limiting to adeno-associated virus (AAV) or pox vectors, or a RNA viral vector of vesicular stomatitis virus (VSV) or a retroviral vector of lentivirus, all of which are known in the art. The viral vectors are frequently used to express proteins of the interest and to make viruses. Various viral vectors are commercially available, which only need insertions of the desired genes for expression. Techniques and reagents required to express interesting proteins and to make viruses with the viral vectors are well known for those skilled in the art. The viral vectors are used to produce defective viruses, which are non-replicating, but each viral genome carries the cloned genes that express HBV neutralizing antibodies or antibody fragments in transduced cells. Procedures for cloning DNA sequence fragments into the viral vectors and for producing defective viruses with the viral vectors in cell culture are well known for those skilled in the art (Balazs et al., 2012).

An AAV was used for expressing anti-HBs antibody(Pan et al., 2008). However, the reported system can't produce sufficiently high level of anti-HBs antibody in vivo. The expressed anti-HBs antibody peaked at 200 mIU/ml, equivalent to 200 ng/ml between week 2 and 7, then declined below 150 ng/ml at week 16. To be effective in neutralizing HBV particles in HBV infected patients, a minimal level of 1-10 µg/ml anti-HBs antibodies is required. This is why the reported system failed to advance to clinical applications. The methods for preparing, cloning and expressing antibody genes are well known for those skilled in the art (Balazs et al., 2012).

Example 8

The long term (longer than 52 weeks) high level (average 100 µg/ml IgG or higher) of neutralizing antibodies to human immunodeficiency virus (HIV), hepatitis C virus (HCV), or influenza virus were expressed after a single injection of AAV2/8 viruses that encoded corresponding neutralizing antibodies(Balazs et al., 2013; Balazs et al., 2012; de Jong et al., 2014).

Figure 6:
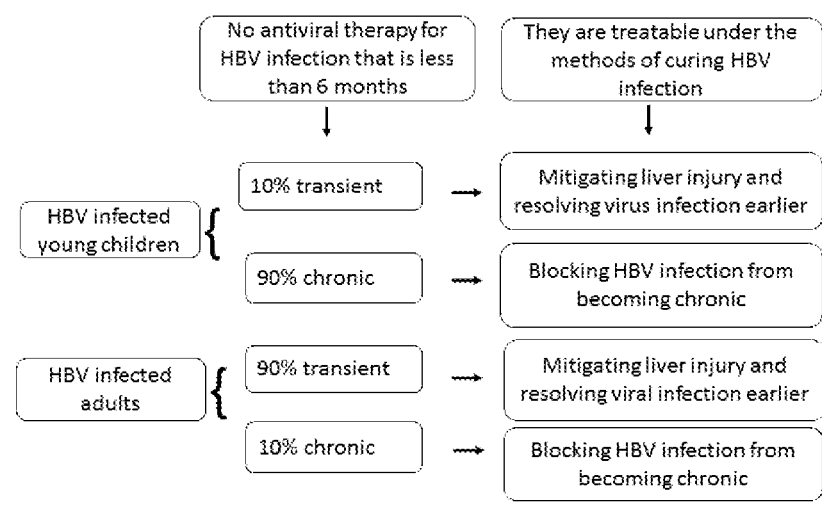

FIG. 6 shows age categories of HBV infected patients who are at acute phase or HBsAg positive for less than 6 months and are not recommended for antiviral therapy in the art, but they become treatable with the methods of curing HBV infection and the single injection of the HBV therapeutics in the inventive subject matter, and expected outcomes after the treatment.

Example 9

There is no recommendation of antiviral treatment for HBV infected patients who are at acute phase of infection or HBsAg positive for less than 6 months in the art. No treatment leaves 90% of infected children and 10% of infected adults chronically infected while it also leaves those who can clear HBV infection a long recovery process.

The methods and the single injection of the HBV therapeutics in the inventive subject matter are used for treating children and adults with HBV infection for less than 6 months. Such treatment will render those HBV infected individuals, who are chronicity-prone, cured of HBV infection, and make the remaining individuals early recovery from HBV infection.

Figure 7:
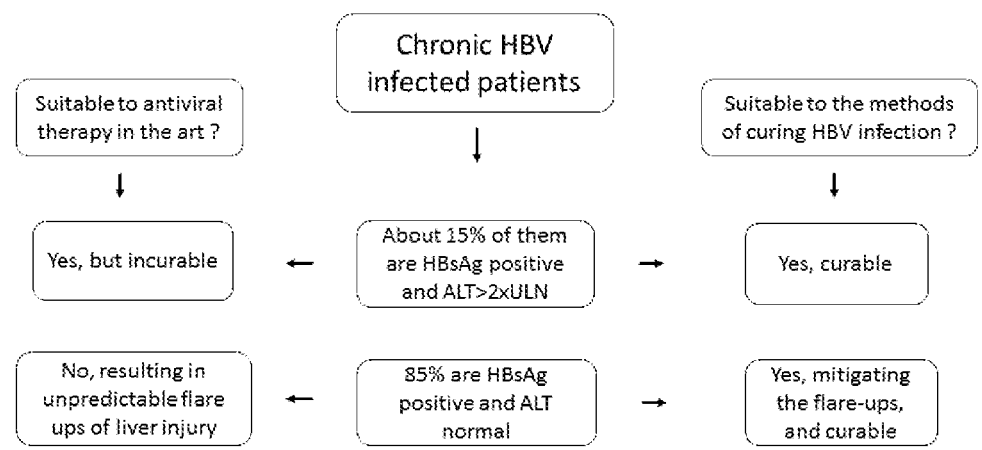

FIG. 7 shows categories of chronic infected patients that are treatable with the methods of curing HBV infection and the single injection of the HBV therapeutics in the inventive subject matter, and expected outcomes after the treatment.

Example 10

Antiviral treatment in the art is recommended for chronic HBV infected patients with elevated ALT and/or histology evidence for liver injury(European Association For The Study Of The, 2012; Liaw et al., 2008; Lok and McMahon, 2009), which only account for 10-15% of chronic HBV infected population. Majority of them are not suitable for the current antiviral treatment. Without antiviral treatment, they can experience unpredictable episodes of flare ups of liver injury that can lead to liver failure with up to 70% mortality (Olson and Kamath, 2011; Sarin et al., 2014). Every single HBV chronic infected patient will become treatable with said methods and through the single injection of the HBV therapeutics in the inventive subject matter as long as HBsAg is positive. The flare ups of liver injury, cirrhosis and liver failure will be gradually eliminated as more and more patients are receiving the treatment with said methods of curing HBV infection.

Figure 8:
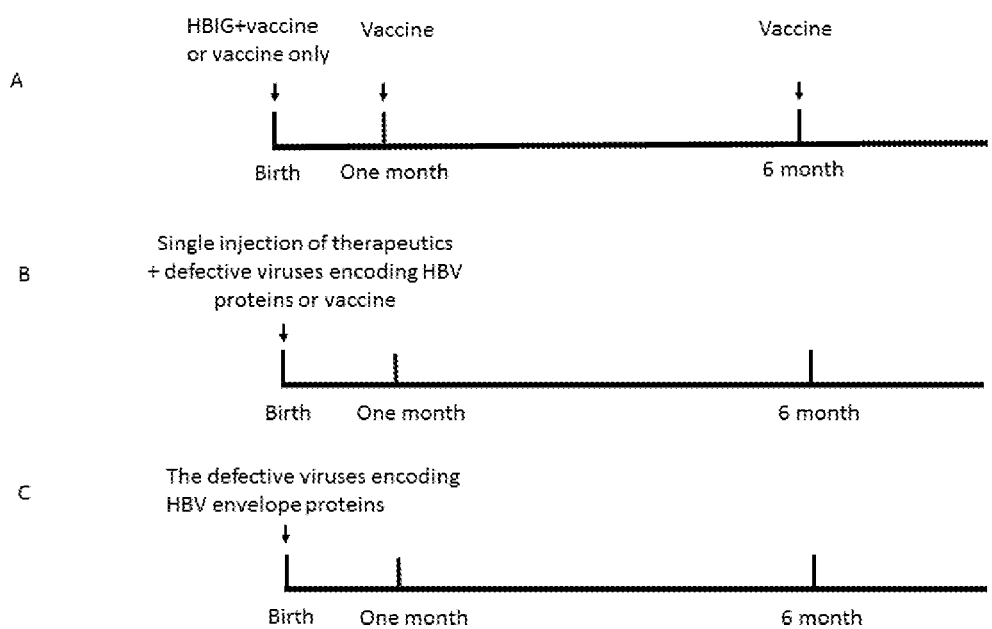

FIG. 8 shows the immunization schedule in the art (A) and two schedules in this invention (B and C). One schedule comprises the single injection of the HBV therapeutics in combination with defective viruses encoding HBV envelope proteins or HBV vaccine for infants borne to HBV positive mothers or individuals with exposure to HBV infection (B); and the other comprises a single injection of the defective viruses encoding HBV envelope proteins for infants borne to HBV negative mothers (C). Both schedules in the present invention reduces 4 injections over three time points in the art, to a single or two injection(s) at a single time point. HBV immunization of newborns or individuals within 24 hours after birth or HBV exposure is recommended, but not required when the single injection of the HBV therapeutics is used.

Example 11

HBV vaccines in the art comprise plasma-derived HBsAg or recombinant HBV envelope proteins, which requires 3 injections because half-life of the administrated viral proteins is short. In preferred embodiments, the HBV vaccines in the art are replaced with the defective viruses that encodes, express and secret sufficient level of HBV envelope proteins for 1-6 months or longer.

The HBV immunization in the art is scheduled at 3 time points: a first injection occurs within 24 hours after birth or immediately after an exposure to HBV infectious materials, then two more injections at 1 and 6 months later. The schedule with multi-injection, not only increases the cost of immunization, but also discourage people from seeking or receiving HBV vaccination, contributing to incomplete coverage of eligible population in developing countries. The methods and the prophylactics for HBV immunization in the inventive subject matter comprise three features: 1). Reduction of 3 or more injections to one or two injections; 2). Reduction of 3 times of injection to a single time of injection; 3). Complete protection.

A simplified schedule with better protection will reduce barriers to access HBV immunization by millions of young children in developing countries where HBV infection is usually endemic.

Figure 9:
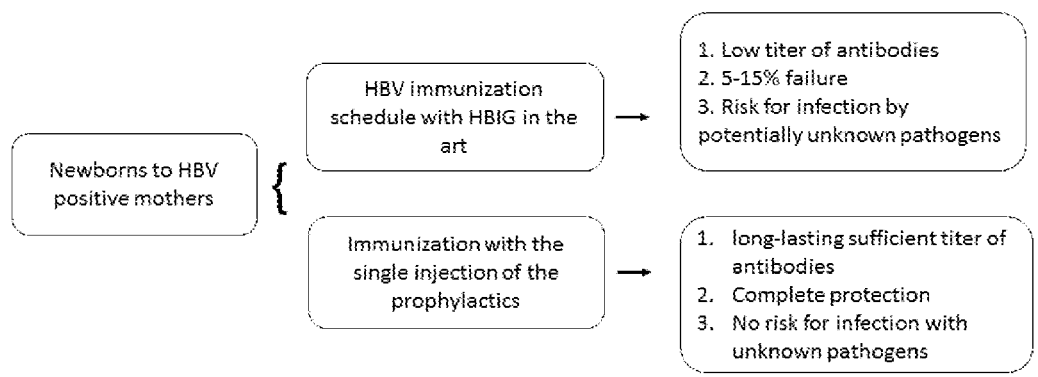

FIG. 9 describes expected outcomes of immunizing newborns with the methods and the HBV therapeutics in the inventive subject matter comparing the HBV immunization in the art.

Example 12

The HBV immunization composition in the art is designed to provide passive (through HBIG) and active (through priming B cells) immunization of infants born to HBV positive mothers against HBV infection. However, the amount of HBV neutralizing antibodies in HBIG is not sufficiently high, variable and it falls quickly because of consumption with neutralization of HBV particles. The HBIG can't completely protect infants from HBV infection when their mothers carried high load of HBV particles (Lee et al., 2006; Zou et al., 2012). This is why 5-15% newborns became chronic HBV infected despite full immunization. To provide the complete protection to newborns or to cure HBV infection in newborns, a sustainable high level of HBV neutralizing antibodies should be expressed or administrated in HBV positive pregnant women. Alternatively, the single injection of the HBV therapeutics can be given to newborns if their mothers miss the treatment with said HBV therapeutics, which produce a long term sufficient level of the anti-HBs antibodies.

As used herein, HBV particles include both full and subviral particles. The full viral particles, also called Dane particles, are virions that are infectious. The subviral particles only consist of HBsAg without the nucleocapsid and viral genome, are not infectious. Both particles carry HBsAg and the serum concentration of HBV particles can be estimated by quantitative detection of HBsAg.

HBV neutralizing antibodies are defined as anti-HBs antibodies that are binding to one or more than one epitope on S, pre-2 or pre-S2 protein of HBsAg or HBV full particles, resulting in a loss of HBV infectiousness.

Antibody fragment is referred to a fab fragment that comprise variable and constant regions of heavy and light chains of an antibody and that contains binding site for a specific antigen.

Complete protection is defined as no failure in protection against HBV infection in an immunized subject with the single injection of the HBV therapeutics and the subject is a newborn or young child or an adult.

Defective viruses, as used herein, are the viruses that are incapable of replicating themselves (non-replicating) in the transduced cells because some or all key elements including the genes encoding viral enzymes and viral proteins required for viral replication are deleted in the viral genomes.

A long term of anti-HBs antibodies expression refers the expression of anti-HBs antibodies for 1-3 months or longer or up to 12 months or longer.

Cure of HBV infection is defined as clear of HBV infection from all infected cells accompanied by loss of serum HBsAg and appearance of the endogenous anti-HBs antibodies after the single injection of the HBV therapeutics that express the long term sufficient amount of HBV neutralizing antibodies or multi injection of the exogenous HBV neutralizing antibodies.

Alanine Aminotransferase (ALT). Normal value: <40IU/L and elevated level:>40 IU/L Early recovery is defined as a clear of HBV infection in a period that is shorter than 6 months in HBV infected individuals.

Children refer a subject younger than 18 years comprising Newborns, Infants, Toddlers, Preschoolers, Middle Childhood, Young Teens and Teenagers. Children who are younger than 5 years, are referred as young children.

Adults refer individuals who are 18 years or older.

Antivirals are defined as therapeutics that act on inhibiting, blocking or disrupting viral lifecycle or degrading viral components (proteins or nucleic acids).

Immunomodulators are defined as molecules or cells or structures that target or regulate components of immunity.

Acute HBV infection refers an initial HBV infection that is featured with appearance of clinical hepatitis manifestations and IgM antibody to hepatitis B core antigen, and positive HBsAg for less than 6 months.

Chronic HBV infection refers a HBV infection that has persisted for more than 6 months, which may or may not have clinical manifestations of viral hepatitis.

HBsAg seroconversion is marked by HBsAg negative and anti-HBs antibody positive.

REFERENCES

Balazs, A., Bloom, J., Hong, C., Rao, D., Baltimore, D., 2013. Broad protection against influenza infection by vectored immunoprophylaxis in mice. Nature biotechnology 31, 647-652.

Balazs, A., Chen, J., Hong, C., Rao, D., Yang, L., Baltimore, D., 2012. Antibody-based protection against HIV infection by vectored immunoprophylaxis. Nature 481, 81-84.

Brunetto, M. R., Giarin, M. M., Oliveri, F., Chiaberge, E., Baldi, M., Alfarano, A., Serra, A., Saracco, G., Verme, G., Will, H., et al. 1991. Wild-type and e antigen-minus hepatitis B viruses and course of chronic hepatitis. Proceedings of the National Academy of Sciences of the United States of America 88, 4186-4190.

CDC, 2005. A Comprehensive Immunization Strategy to Eliminate Transmission of Hepatitis B Virus Infection in the United States Recommendations of the Advisory Committee on Immunization Practices (ACIP) Part 1: Immunization of Infants, Children, and Adolescents.

Chen, H. -L., Lee, C. -N., Chang, C. -H., Ni, Y. -H., Shyu, M. -K., Chen, S. -M., Hu, J. -J., Lin, H., Zhao, L. -L., Mu, S. -C., Lai, M. -W., Tsai, M. -S., Hsu, J. -J., Chen, D. -S., Chan, K. A., Chang, M. -H., 2015. Efficacy of maternal tenofovir disoproxil fumarate in interrupting mother-to-infant transmission of hepatitis B virus. Hepatology 62, 375-386.

Chisari, F. V., Ferrari, C., 1995. Hepatitis B virus immunopathology. Springer seminars in immunopathology 17, 261-281.

Chisari, F. V., Isogawa, M., Wieland, S. F., 2010. Pathogenesis of hepatitis B virus infection. Pathologie-biologie 58, 258-266.

Couillin, I., Pol, S., Mancini, M., Driss, F., Brechot, C., Tiollais, P., Michel, M. L., 1999. Specific vaccine therapy in chronic hepatitis B: induction of T cell proliferative responses specific for envelope antigens. The Journal of infectious diseases 180, 15-26.

de Jong, Y. P., Dorner, M., Mommersteeg, M. C., Xiao, J. W., Balazs, A. B., Robbins, J. B., Winer, B. Y., Gerges, S., Vega, K., Labitt, R. N., Donovan, B. M., Giang, E., Krishnan, A., Chiriboga, L., Charlton, M. R., Burton, D. R., Baltimore, D., Law, M., Rice, C. M., Ploss, A., 2014. Broadly neutralizing antibodies abrogate established hepatitis C virus infection. Science translational medicine 6, 254ra129.

Eren, R., Ilan, E., Nussbaum, O., Lubin, I., Terkieltaub, D., Arazi, Y., Ben-Moshe, O., Kitchinzky, A., Berr, S., Gopher, J., Zauberman, A., Galun, E., Shouval, D., Daudi, N., Eid, A., Jurim, O., Magnius, L. O., Hammas, B., Reisner, Y., Dagan, S., 2000. Preclinical evaluation of two human anti-hepatitis B virus (HBV) monoclonal antibodies in the HBV-trimera mouse model and in HBV chronic carrier chimpanzees. Hepatology 32, 588-596.

European Association For The Study Of The, L., 2012. EASL clinical practice guidelines: Management of chronic hepatitis B virus infection. Journal of hepatology 57, 167-185.

Franco, E., Bagnato, B., Marino, M. G., Meleleo, C., Serino, L., Zaratti, L., 2012. Hepatitis B: Epidemiology and prevention in developing countries. World journal of hepatology 4, 74-80.

Galun, E., Eren, R., Safadi, R., Ashour, Y., Terrault, N., Keeffe, E. B., Matot, E., Mizrachi, S., Terkieltaub, D., Zohar, M., Lubin, I., Gopher, J., Shouval, D., Dagan, S., 2002. Clinical evaluation (phase I) of a combination of two human monoclonal antibodies to HBV: safety and antiviral properties. Hepatology 35, 673-679.

Ganem, D., Prince, A. M., 2004. Hepatitis B virus infection—natural history and clinical consequences. The New England journal of medicine 350, 1118-1129.

Gerlich, W. H., Glebe, D., Schuttler, C. G., 2007. Deficiencies in the standardization and sensitivity of diagnostic tests for hepatitis B virus. Journal of viral hepatitis 14 Suppl 1, 16-21.

Ghany, M. G., Doo, E. C., 2009. Antiviral resistance and hepatitis B therapy. Hepatology 49, S174-184.

Habib, S., Shaikh, O. S., 2007. Hepatitis B immune globulin. Drugs of today 43, 379-394.

Heijtink, R. A., van Nunen, A. B., van Bergen, P., Ostberg, L., Osterhaus, A. D., de Man, R. A., 2001. Administration of a human monoclonal antibody (TUVIRUMAB) to chronic hepatitis B patients pre-treated with lamivudine: monitoring of serum TUVIRUMAB in immune complexes. Journal of medical virology 64, 427-434.

Kosinska, A. D., Zhang, E., Lu, M., Roggendorf, M., 2010. Therapeutic vaccination in chronic hepatitis B: preclinical studies in the woodchuck. Hepatitis research and treatment 2010, 817580.

Kwon, H., Lok, A. S., 2011. Hepatitis B therapy. Nature reviews. Gastroenterology & hepatology 8, 275-284.

Lamberth, J., Reddy, S., Pan, J. -J., Dasher, K., 2015. Chronic hepatitis B infection in pregnancy. World journal of hepatology 7, 1233-1237.

Lee, C., Gong, Y., Brok, J., Boxall, E. H., Gluud, C., 2006. Effect of hepatitis B immunisation in newborn infants of mothers positive for hepatitis B surface antigen: systematic review and meta-analysis. Bmj 332, 328-336.

Liaw, Y. F., Leung, N., Kao, J. H., Piratvisuth, T., Gane, E., Han, K. H., Guan, R., Lau, G. K., Locarnini, S., Chronic Hepatitis, B.G.W.P.o.t.A.-P.A.f.t.S.o.t.L., 2008. Asian-Pacific consensus statement on the management of chronic hepatitis B: a 2008 update. Hepatology international 2, 263-283.

Locarnini, S., Bowden, S., 2010. Drug resistance in antiviral therapy. Clinics in liver disease 14, 439-459.

Lok, A. S., McMahon, B. J., 2009. Chronic hepatitis B: update 2009. Hepatology 50, 661-662.

Lozano, R., Naghavi, M., Foreman, K., Lim, S., Shibuya, K., Aboyans, V., Abraham, J., Adair, T., Aggarwal, R., Ahn, S. Y., Alvarado, M., Anderson, H. R., Anderson, L. M., Andrews, K. G., Atkinson, C., Baddour, L. M., Barker-Collo, S., Bartels, D. H., Bell, M. L., Benjamin, E. J., Bennett, D., Bhalla, K., Bikbov, B., Bin Abdulhak, A., Birbeck, G., Blyth, F., Bolliger, I., Boufous, S., Bucello, C., Burch, M., Burney, P., Carapetis, J., Chen, H., Chou, D., Chugh, S. S., Coffeng, L. E., Colan, S. D., Colquhoun, S., Colson, K. E., Condon, J., Connor, M. D., Cooper, L. T., Corriere, M., Cortinovis, M., de Vaccaro, K. C., Couser, W., Cowie, B. C., Criqui, M. H., Cross, M., Dabhadkar, K. C., Dahodwala, N., De Leo, D., Degenhardt, L., Delossantos, A., Denenberg, J., Des Jarlais, D. C., Dharmaratne, S. D., Dorsey, E. R., Driscoll, T., Duber, H., Ebel, B., Erwin, P. J., Espindola, P., Ezzati, M., Feigin, V., Flaxman, A. D., Forouzanfar, M. H., Fowkes, F. G., Franklin, R., Fransen, M., Freeman, M. K., Gabriel, S. E., Gakidou, E., Gaspari, F., Gillum, R. F., Gonzalez-Medina, D., Halasa, Y. A., Haring, D., Harrison, J. E., Havmoeller, R., Hay, R. J., Hoen, B., Hotez, P. J., Hoy, D., Jacobsen, K. H., James, S. L., Jasrasaria, R., Jayaraman, S., Johns, N., Karthikeyan, G., Kassebaum, N., Keren, A., Khoo, J. P., Knowlton, L. M., Kobusingye, O., Koranteng, A., Krishnamurthi, R., Lipnick, M., Lipshultz, S. E., Ohno, S. L., Mabweijano, J., MacIntyre, M. F., Mallinger, L., March, L., Marks, G. B., Marks, R., Matsumori, A., Matzopoulos, R., Mayosi, B. M., McAnulty, J. H., McDermott, M. M., McGrath, J., Mensah, G. A., Merriman, T. R., Michaud, C., Miller, M., Miller, T. R., Mock, C., Mocumbi, A. O., Mokdad, A. A., Moran, A., Mulholland, K., Nair, M. N., Naldi, L., Narayan, K. M., Nasseri, K., Norman, P., O'Donnell, M., Omer, S. B., Ortblad, K., Osborne, R., Ozgediz, D., Pahari, B., Pandian, J. D., Rivero, A. P., Padilla, R. P., Perez-Ruiz, F., Perico, N., Phillips, D., Pierce, K., Pope, C. A., 3rd, Porrini, E., Pourmalek, F., Raju, M., Ranganathan, D., Rehm, J. T., Rein, D. B., Remuzzi, G., Rivara, F. P., Roberts, T., De Leon, F. R., Rosenfeld, L. C., Rushton, L., Sacco, R. L., Salomon, J. A., Sampson, U., Sanman, E., Schwabel, D. C., Segui-Gomez, M., Shepard, D. S., Singh, D., Singleton, J., Sliwa, K., Smith, E., Steer, A., Taylor, J. A., Thomas, B., Tleyjeh, I. M., Towbin, J. A., Truelsen, T., Undurraga, E. A., Venketasubramanian, N., Vijayakumar, L., Vos, T., Wagner, G. R., Wang, M., Wang, W., Watt, K., Weinstock, M. A., Weintraub, R., Wilkinson, J. D., Woolf, A. D., Wulf, S., Yeh, P. H., Yip, P., Zabetian, A., Zheng, Z. J., Lopez, A. D., Murray, C. J., AlMazroa, M. A., Memish, Z. A., 2012. Global and regional mortality from 235 causes of death for 20 age groups in 1990 and 2010: a systematic analysis for the Global Burden of Disease Study 2010. Lancet 380, 2095-2128.

McMahon, G., Ehrlich, P. H., Moustafa, Z. A., McCarthy, L. A., Dottavio, D., Tolpin, M. D., Nadler, P. I., Ostberg, L., 1992. Genetic alterations in the gene encoding the major HBsAg: DNA and immunological analysis of recurrent HBsAg derived from monoclonal antibody-treated liver transplant patients. Hepatology 15, 757-766.

Okamoto, H., Tsuda, F., Akahane, Y., Sugai, Y., Yoshiba, M., Moriyama, K., Tanaka, T., Miyakawa, Y., Mayumi, M., 1994. Hepatitis B virus with mutations in the core promoter for an e antigen-negative phenotype in carriers with antibody to e antigen. Journal of virology 68, 8102-8110.

Olson, J., Kamath, P., 2011. Acute-on-chronic liver failure: concept, natural history, and prognosis. Current opinion in critical care 17, 165-169.

Pan, C. Q., Lee, H. M., 2013. Antiviral therapy for chronic hepatitis B in pregnancy. Seminars in liver disease 33, 138-146.

Pan, T., Cai, M., Tang, L., Zhou, L. Q., Li, B. J., Zhu, T., Li, H. Z., Li, S. Y., Xiao, X., Chen, Z. S., 2008. A novel approach of prophylaxis to HBV recurrence after liver transplantation. Virology 382, 1-9.

Patient, R., Hourioux, C., Roingeard, P., 2009. Morphogenesis of hepatitis B virus and its subviral envelope particles. Cellular microbiology 11, 1561-1570.

Pult, I., Abbott, N., Zhang, Y. Y., Summers, J., 2001. Frequency of spontaneous mutations in an avian hepadnavirus infection. Journal of virology 75, 9623-9632.

Sarin, S., Kedarisetty, C., Abbas, Z., Amarapurkar, D., Bihari, C., Chan, A., Chawla, Y., Dokmeci, A. K., Garg, H., Ghazinyan, H., Hamid, S., Kim, D., Komolmit, P., Lata, S., Lee, G., Lesmana, L., Mahtab, M., Maiwall, R., Moreau, R., Ning, Q., Pamecha, V., Payawal, D., Rastogi, A., Rahman, S., Rela, M., Saraya, A., Samuel, D., Saraswat, V., Shah, S., Shiha, G., Sharma, B., Sharma, M., Sharma, K., Butt, A., Tan, S., Vashishtha, C., Wani, Z., Yuen, M.-F., Yokosuka, O., 2014. Acute-on-chronic liver failure: consensus recommendations of the Asian Pacific Association for the Study of the Liver (APASL) 2014. Hepatology international 8, 453-471.

Thermet, A., Buronfosse, T., Werle-Lapostolle, B., Chevallier, M., Pradat, P., Trepo, C., Zoulim, F., Cova, L., 2008. DNA vaccination in combination or not with lamivudine treatment breaks humoral immune tolerance and enhances cccDNA clearance in the duck model of chronic hepatitis B virus infection. The Journal of general virology 89, 1192-1201.

Trepo, C., Chan, H. L., Lok, A., 2014. Hepatitis B virus infection. Lancet 384, 2053-2063. WHO, 2015. Hepatitis B.

Yamamoto, K., Horikita, M., Tsuda, F., Itoh, K., Akahane, Y., Yotsumoto, S., Okamoto, H., Miyakawa, Y., Mayumi, M., 1994. Naturally occurring escape mutants of hepatitis B virus with various mutations in the S gene in carriers seropositive for antibody to hepatitis B surface antigen. Journal of virology 68, 2671-2676.

Zhang, Y. Y., Summers, J., 1999. Enrichment of a precore-minus mutant of duck hepatitis B virus in experimental mixed infections. Journal of virology 73, 3616-3622.

Zhang, Y. Y., Summers, J., 2004. Rapid production of neutralizing antibody leads to transient hepadnavirus infection. Journal of virology 78, 1195-1201.

Zou, H., Chen, Y., Duan, Z., Zhang, H., Pan, C., 2012. Virologic factors associated with failure to passive-active immunoprophylaxis in infants born to HBsAg-positive mothers. Journal of viral hepatitis 19, e18-25.

What is claimed is:

1. A method of treating chronic HBV infection and providing protection against recurrence of HBV infection in a human patient, comprising:
   a. measuring the level of the serum HBV particles in the HBV infected human patient;
   b. administering to the HBV infected human patient a composition comprising HBV therapeutic vectors comprising nucleic acid sequences encoding HBV neutralizing antibodies or antibody fragments to endogenously express the HBV neutralizing antibodies at a level that is higher than the level of the serum HBV particles in the HBV infected human patient, wherein said level of HBV neutralizing antibodies result in a level of undetectable HBV particles in serum or a full HBsAg seroconversion from HBsAg positive to anti-HBs antibody positive; and
   c. optionally, further administering to the HBV infected human patient with a single time injection of the HBV therapeutic vectors comprising nucleic acid sequences encoding HBV neutralizing antibodies or antibody fragments to endogenously express the HBV neutralizing antibodies as prophylactics at a level that is higher than the level of the serum HBV particles in the HBV infected human patient to prevent recurrence of HBV infection.

2. The method of claim 1, wherein the HBV neutralizing antibodies is at a level of 1-100 μg/ml in the patient's blood for three months or longer.

3. The method of claim 1, wherein the treating of chronic HBV infection comprises treating newborns/children who are HBV infected.

4. The method of claim 1, wherein the treating of chronic HBV infection comprises treating adults who are HBV infected.

5. The method of claim 1, wherein the HBV infected subjects are chronic HBV infected individuals who are HBsAg positive for more than 6 months having normal or elevated alanine aminotransferase (ALT) level.

6. The method of claim 1, wherein the HBV infected human patient comprise HBV positive pregnant women, and organ transplant recipients who are HBsAg positive or HBsAg negative/anti hepatitis B core antibody (anti-HBc) positive, and are prone to recurrent HBV infection after the transplant.

7. The method of claim 1, wherein the HBV therapeutic vectors comprise a mixed population of vectors each of which encodes one specific anti-HBs antibody or antibody fragment binding to one or more epitopes of HBV envelope proteins, or comprise a single vectors population encoding one HBV neutralizing antibody or antibody fragment binding to one or more epitopes of HBV envelope proteins.

8. The method of claim 1, wherein the HBV therapeutic vectors constantly express and secret HBV neutralizing antibodies at a level of 1-100 μg/ml in the patient's blood for six months or longer.

9. The method of claim 8, wherein the HBV therapeutic vectors function as prophylactics.

10. The method of claim 1, wherein the single injection of HBV therapeutic vectors or the multi-injection of exogenous HBV neutralizing antibodies is applied in a monotherapy.

11. The method of claim 1, wherein the single injection of HBV therapeutics or the multi-injection of exogenous HBV neutralizing antibodies is applied in combination with other antivirals and/or immunomodulators.

12. The method of claim 11, wherein the other antivirals and/or immunomodulators comprise nucleotide analogues (NAs), capsid inhibitors, ligands to HBV receptors, siRNA drugs, interferons/cytokines and thymosin.

* * * * *